United States Patent [19]

Shivkumar

[11] Patent Number: 5,755,997
[45] Date of Patent: May 26, 1998

[54] CHIRAL COMPOUNDS WITH LIQUID CRYSTALLINE NATURE

[75] Inventor: Bagavant Shivkumar, Suwon, Rep. of Korea

[73] Assignee: Samsung Display Devices Co., Ltd., Kyungki-do, Rep. of Korea

[21] Appl. No.: 720,874

[22] Filed: Oct. 3, 1996

[51] Int. Cl.$^6$ .............................. C09K 19/12; C07C 69/72
[52] U.S. Cl. ........................ 252/299.65; 560/65; 560/83
[58] Field of Search ...................... 252/299.65; 560/65, 560/83

[56] References Cited

PUBLICATIONS

CA 112: 188070, "Optical anisotropies of nematogens from the depolarized Rayleigh spectra", Floudas et al., 1990

CA 115: 40423, "Magnetic susceptibility and order parameter of nematic liquid crystals s determined by a high-temperature Squid magnetometer", Dries et al., 1991.

CA 126: 11772, "Preparation of 3–methyladipic aid diesters and liquid crystals composition containing them", Nishama et al, 1997.

*Primary Examiner*—Shean C. Wu
*Attorney, Agent, or Firm*—Birch, Stewart, Kolasch & Birch, LLP

[57] ABSTRACT

Compounds of the following formula exhibit broad chiral smectic C phases and have excellent stability:

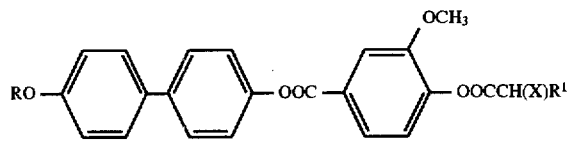

wherein R represents a hydrocarbon group having 1 to 14 carbon atoms, X is a halogen atom, and $R^1$ represents a branched alkyl group having 3 to 8 carbon atoms.

10 Claims, 10 Drawing Sheets

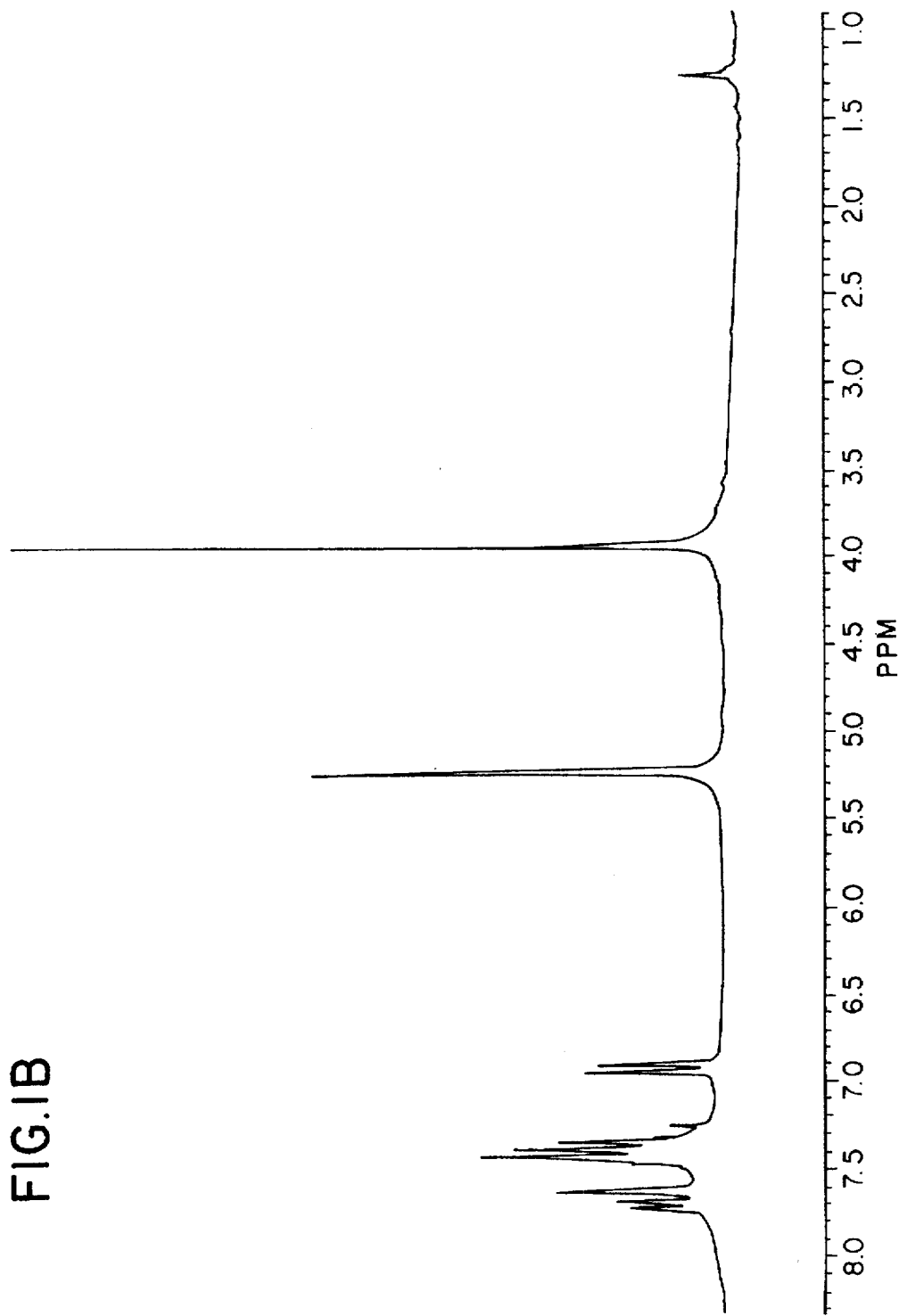

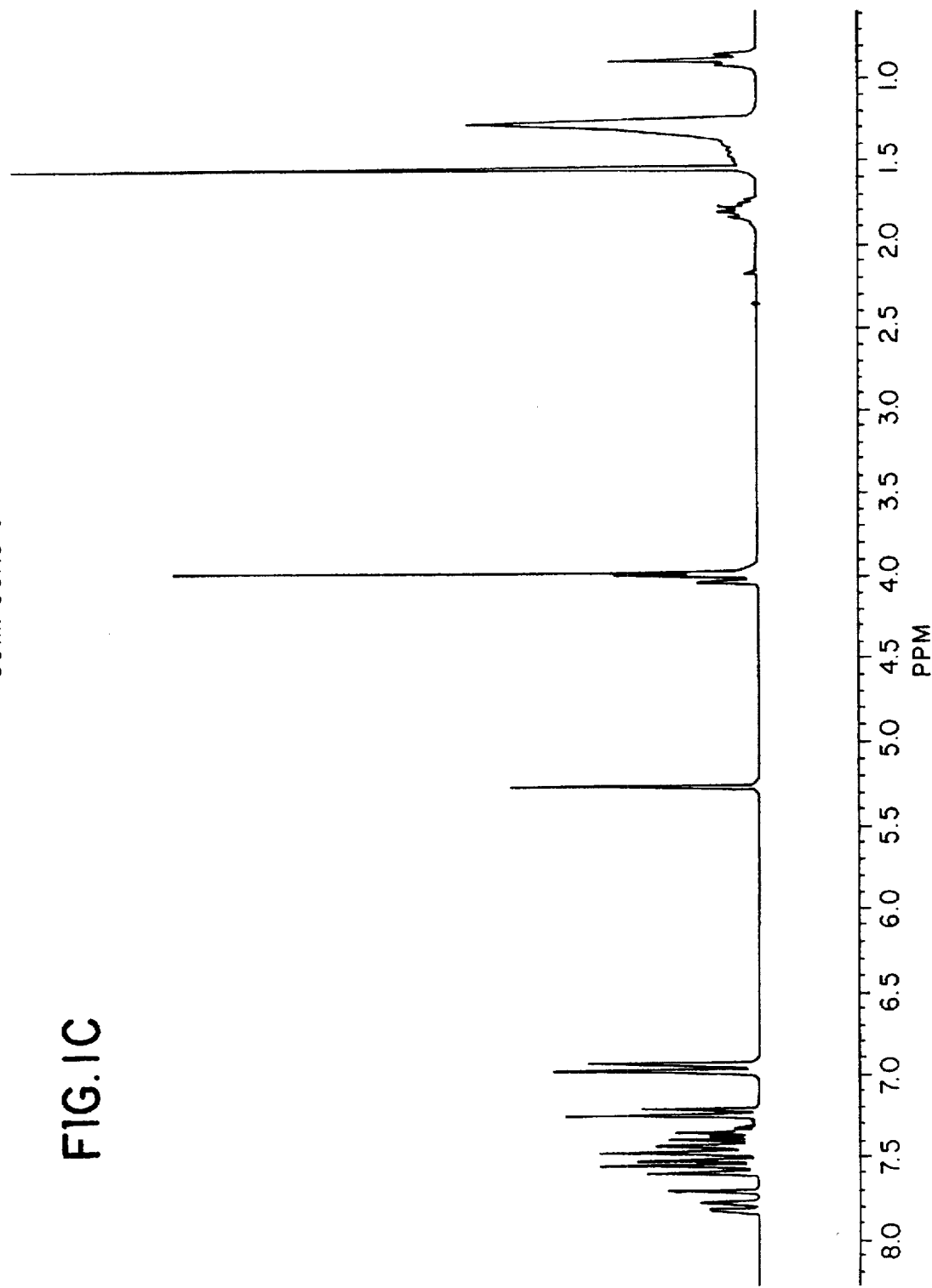

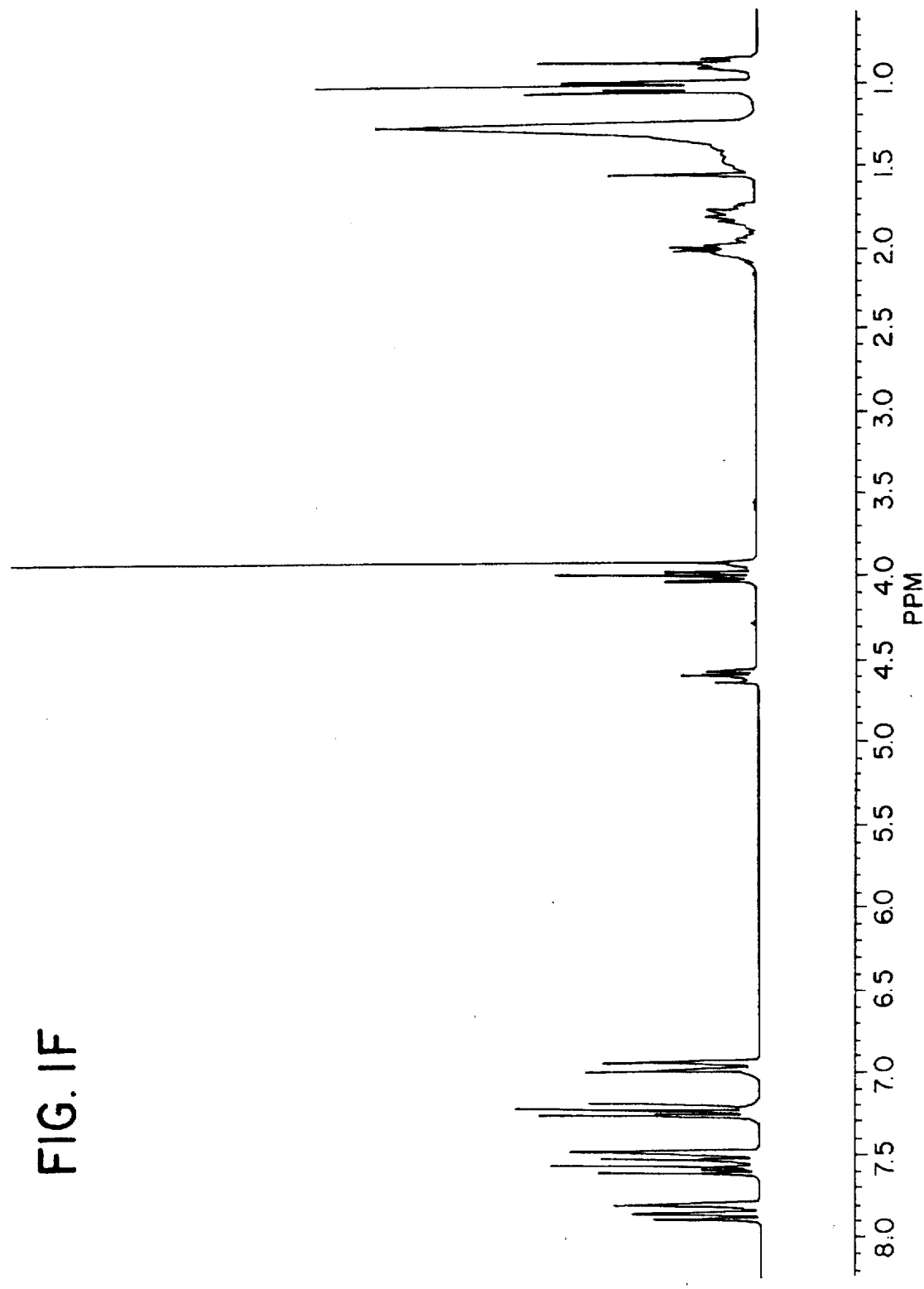
FIG. IF

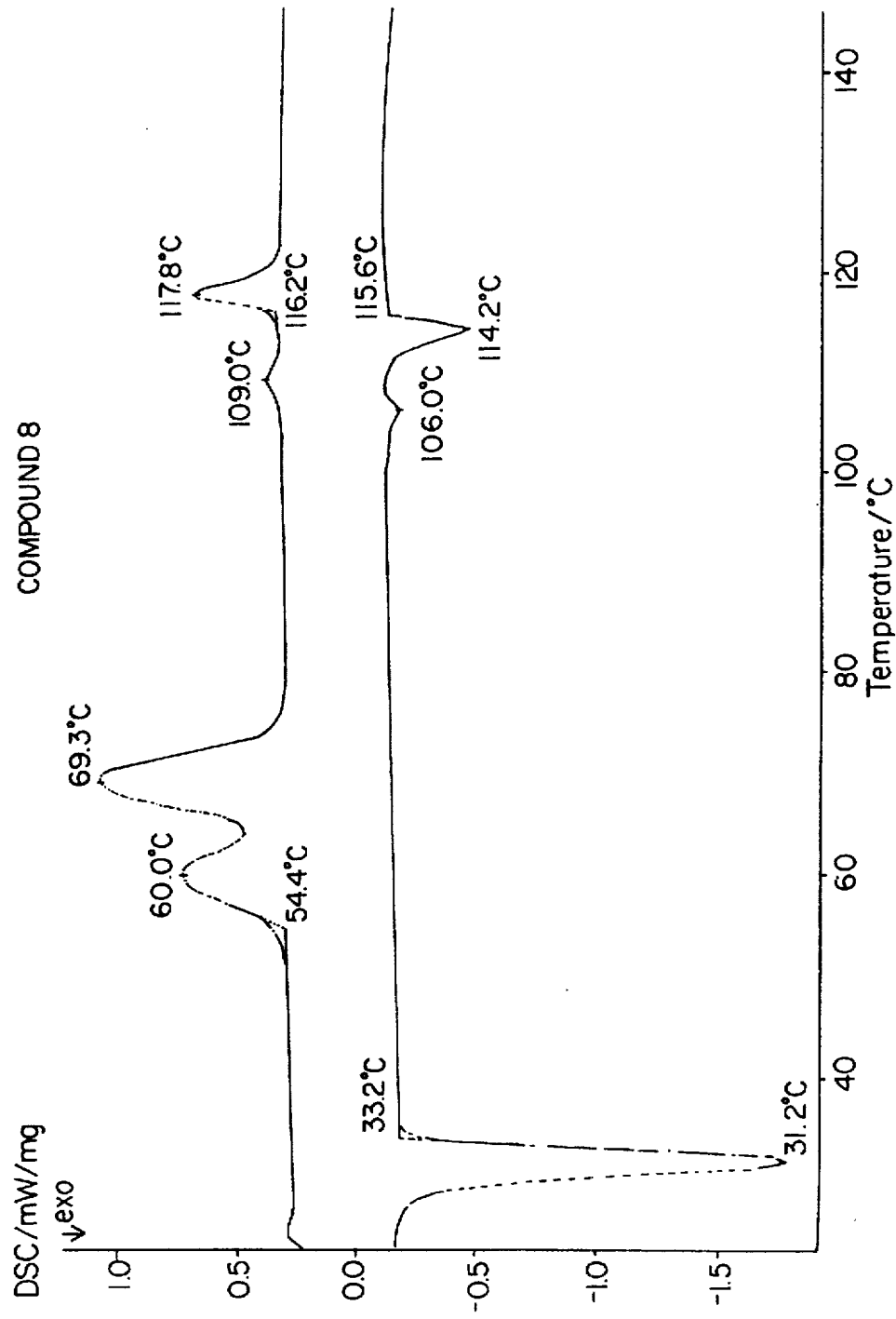

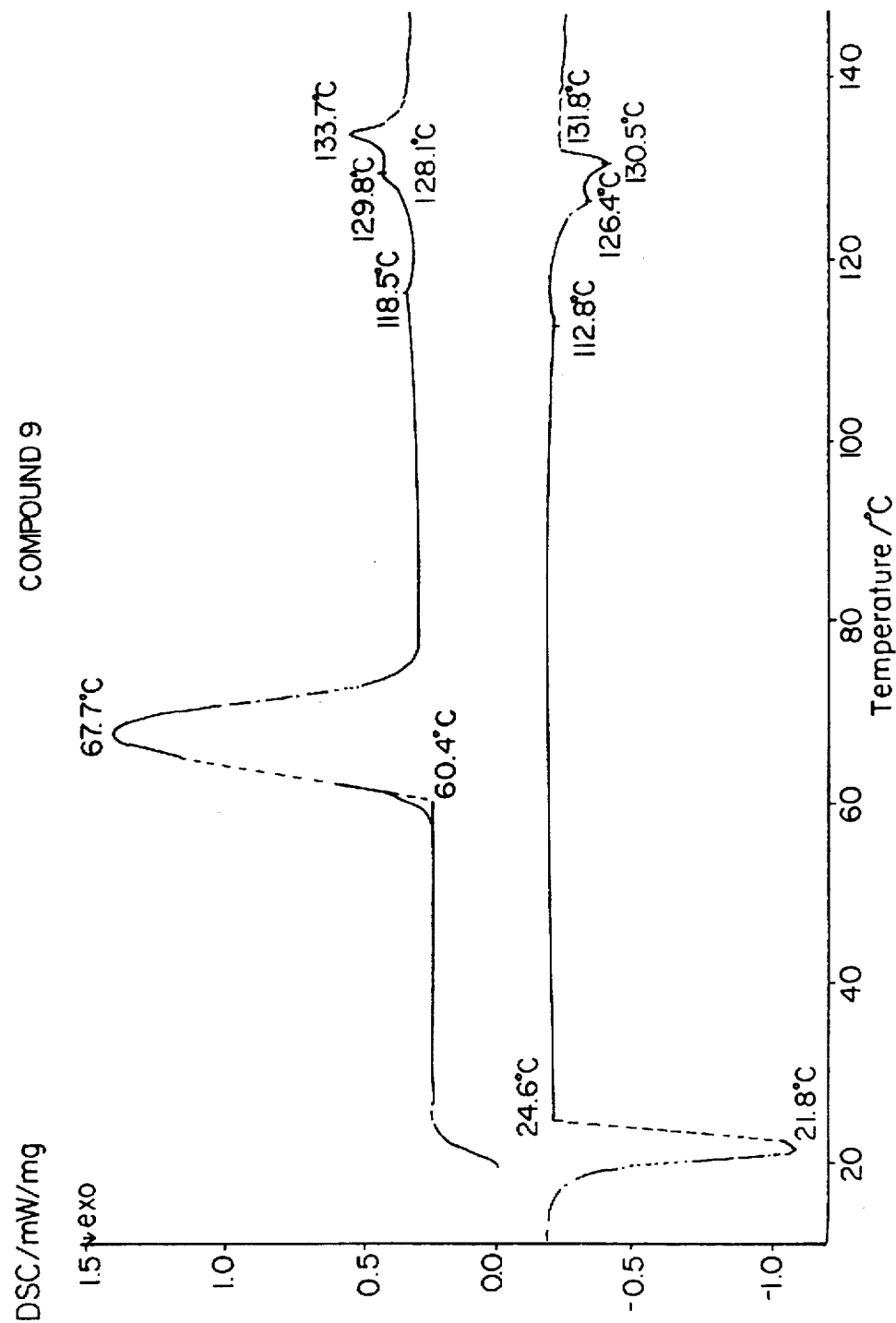

CHIRAL COMPOUNDS WITH LIQUID CRYSTALLINE NATURE

BACKGROUND OF THE INVENTION

1. Field of the Invention

This invention relates to the synthesis of novel compounds that exhibit the chiral smectic C phase [$S_c$*] and thus are suitable for use in ferroelectric liquid crystal devices.

2. Description of the Prior Art

Organic compounds in their liquid crystalline phases offer an electro-active media that interacts with light in a systematic manner. This electro-optic property has been used in the construction of display devices. The structural requirements of the organic compounds used vary according to the phase and the type of the device. In 1975 symmetry arguments were presented for the existence of ferroelectricity in tilted smectic phases comprised of chiral molecules. [R. B. Meyer, L. Liebert, L. Strzelecki, and P. Keller *J. Phys. (Paris) Lett.* 36 L-69.] Later an electro-optical effect that utilized the ferroelectric property was demonstrated in 1980 [N. A. Clark and S. T. Lagerwall, *Appl. Phys. Lett.* 36, 899.]

The main advantage of these bistable devices over the conventional nematic technologies rests in the fact that their switching times are one hundred to one thousand times faster. The chiral smectic C phase is the most fluid phase to have such a property and hence synthesis of compounds exhibiting this phase has gained importance in the industry. The compounds must have a chemical, photochemical, thermal and electrical stability in addition to possessing a wide range of the smectic C* phase in order to be useful. A smectic A phase following the C* phase is found to improve the quality of the alignment and hence is also desirable.

These and other required properties have been translated, albeit only in a qualitative manner, into structural parameters. Thus, a normal alkyl chain of eight to twelve methylene units attached through an ether linkage to a core comprised of two to three aromatic rings with conjugating bridging groups and a chiral moiety with a branched alkyl chain often substituted with groups which would enhance the lateral dipole and hinder the rotation of the chiral carbon about the long axis of the molecule, form common features in the compounds exhibiting a smectic C* phase. Efforts in search of novel compounds exhibiting this phase have resulted in structures with heterocyclic cores to lower viscosity and the incorporation of strong electronegative groups such as the cyano group at the chiral carbon to enhance the lateral dipole. [U.S. Pat Nos. 5,389,290; 5,380,460; 5,486,309] However, optimization of the properties required has been more easily achieved by the use of mixtures of different compounds exhibiting the smectic C* phase and since it was shown [W. Kuczynski and H. Stegemeyer, *Chem. Phys. Lett.*, 70, 123 (1980)] that a smectic C phase doped with chiral molecules gave a ferroelectric phase, this result has now been extensively applied to other systems [U.S. Pat. No. 5,378,394; 5,439,612] as well.

Thus, the prior art compounds are not entirely satisfactory. Specifically, the prior art chiral compounds fail to meet all of the above-identified requirements simultaneously.

SUMMARY OF THE INVENTION

Accordingly, it is an object of the present invention to provide new compounds that exhibit a chiral smectic C phase over a broad temperature range and that exhibit good stability.

These and other objects of the present invention are achieved by compounds represented by the following formula:

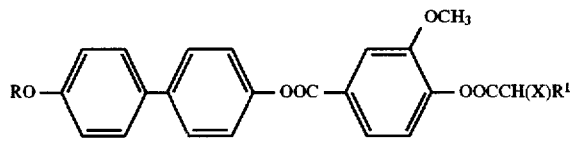

wherein R represents a hydrocarbon group having 1 to 14 carbon atoms, X is a halogen atom, and $R^1$ represents a branched alkyl group having 3 to 8 carbon atoms.

BRIEF DESCRIPTION OF THE DRAWINGS

FIGS. 1a, 1b, 1c, 1d, 1e, 1f, and 1g show proton magnetic resonance plots of compounds [2], [3], [5], [6], [7], [8], and [9], respectively.

FIGS. 2a, 2b, and 2c show differential scanning calorimetry (D.S.C.) scans of compounds [7], [8], and [9], respectively.

DETAILED DESCRIPTION OF INVENTION

Figure 1A:
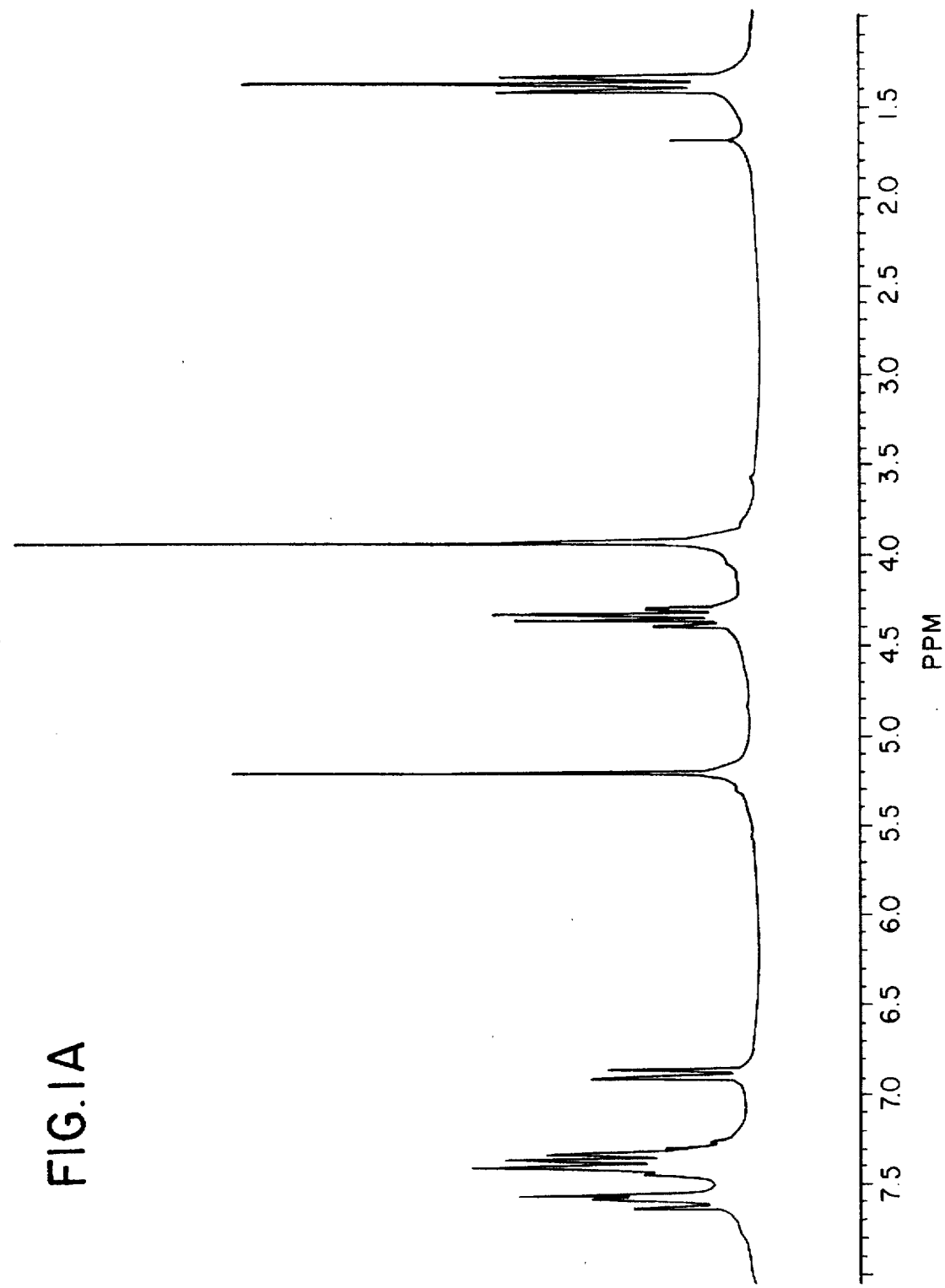
Figure 1D:
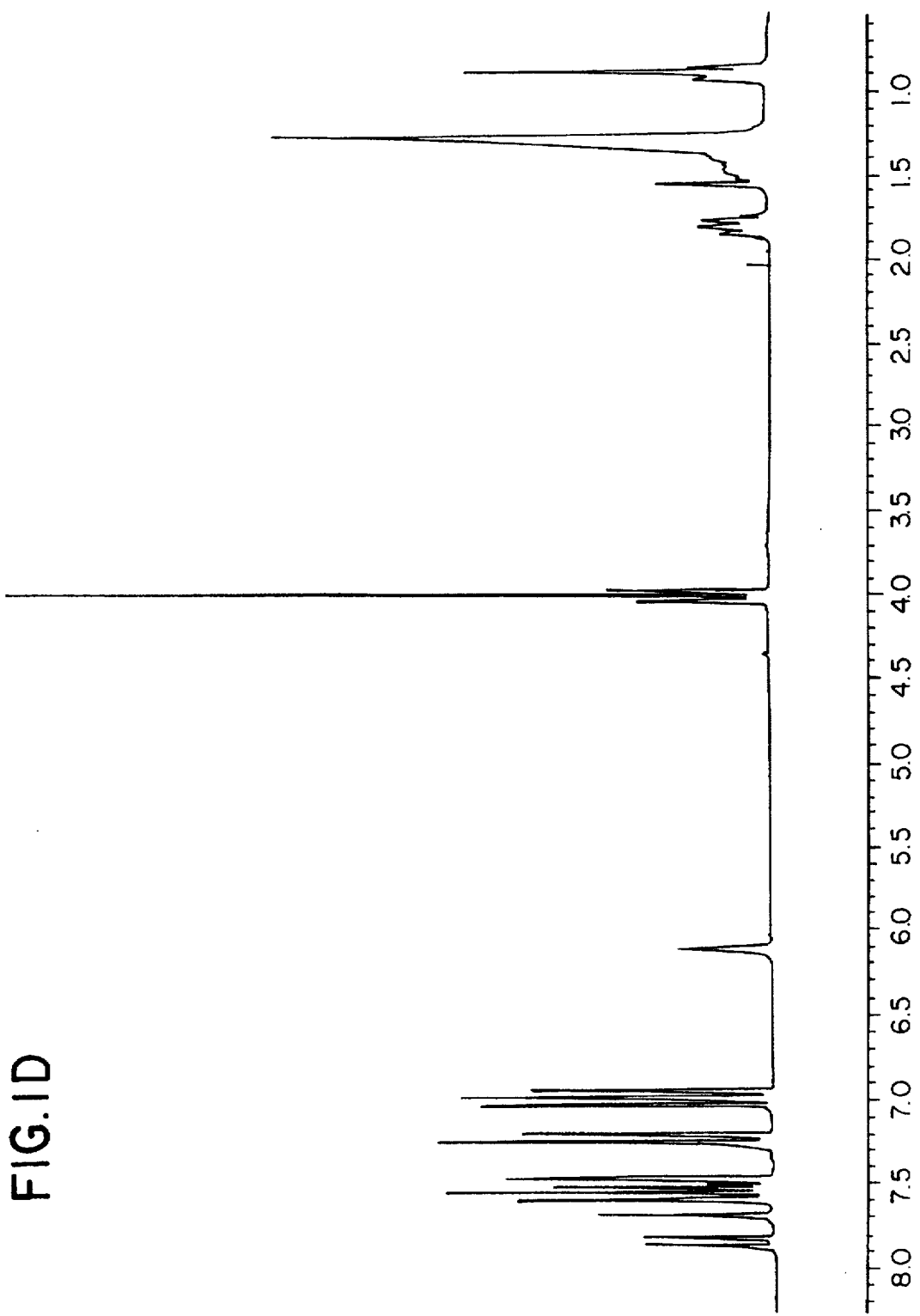
Figure 1E:
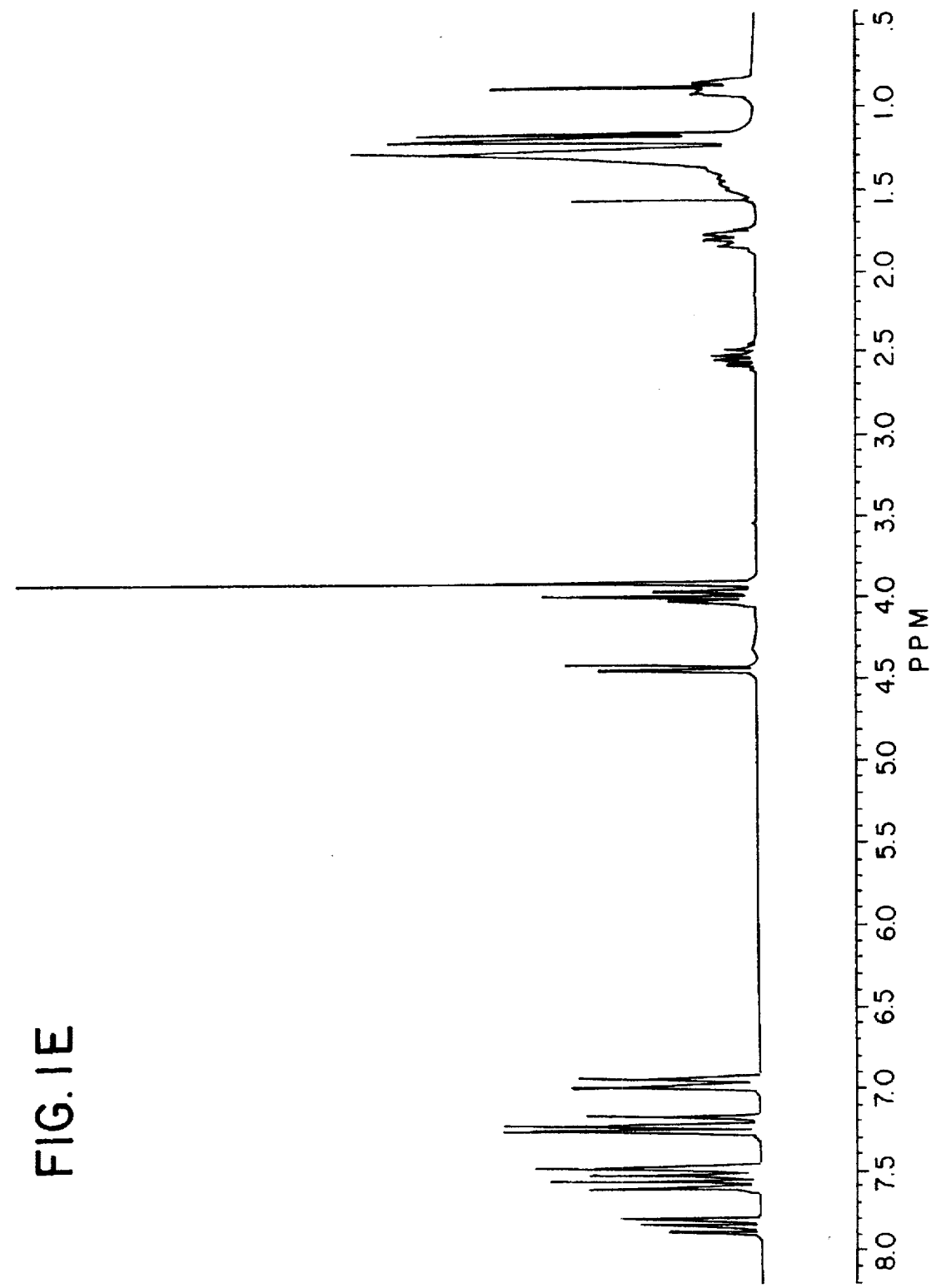
Figure 1G:
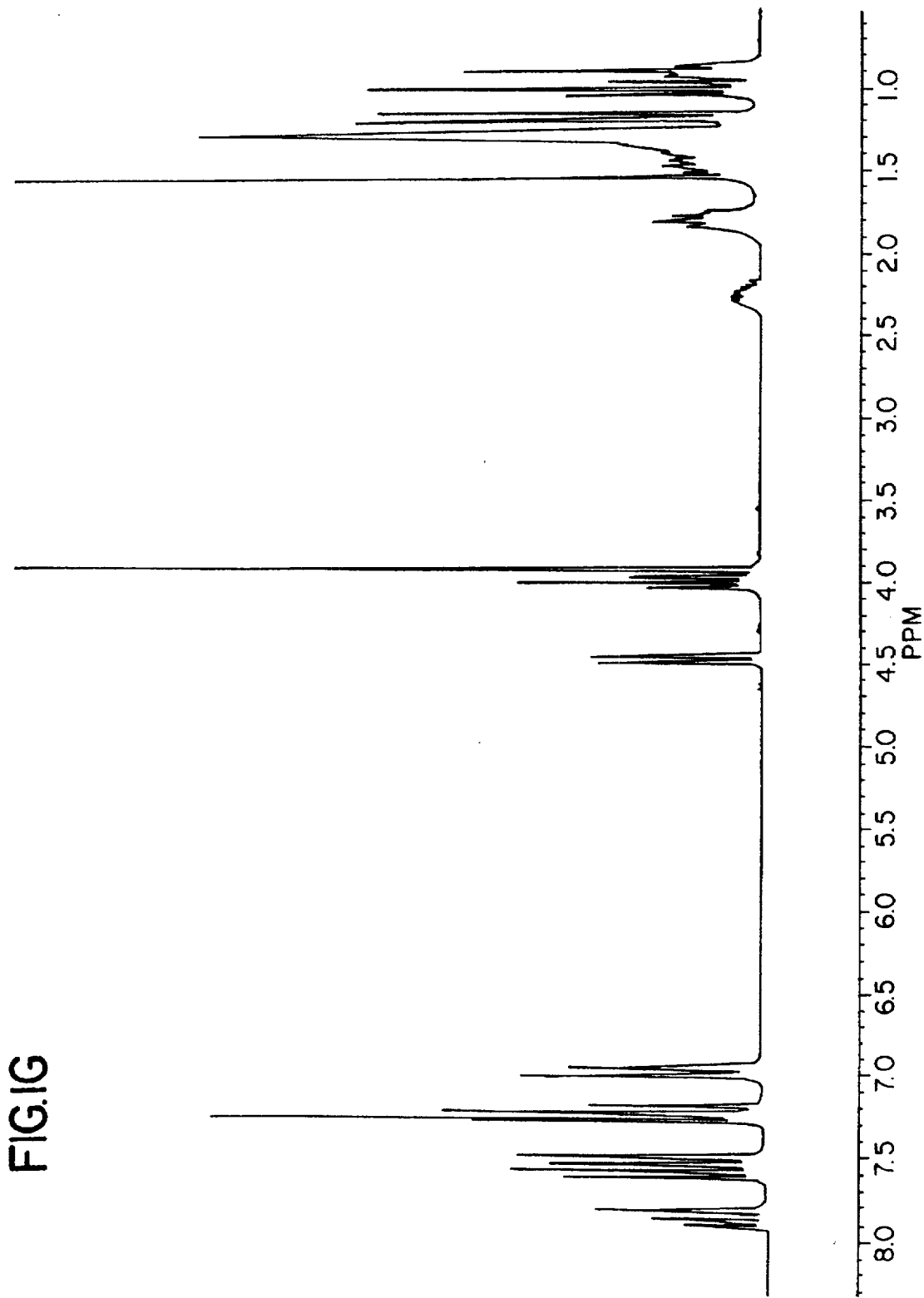

The compounds of the present invention are represented by the formula:

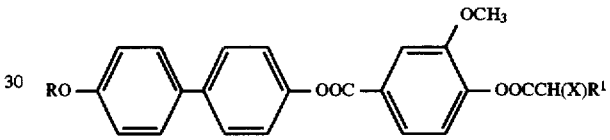

R represents a hydrocarbon group having 1 to 14 carbon atoms. Preferably, R represents a straight chain alkyl group having 1–14 carbon atoms, more preferably 6–12 carbons. X represents a halogen atom (F, Br, Cl, or I) and is preferably chlorine. $R^1$ represents a branched alkyl group having from 3 to 8 carbon atoms, preferably 3, 4 or 5 carbon atoms. While multiple branching is contemplated to be within the scope of the present invention, single branching is preferred. In one embodiment $R^1$ contains a methyl group as the sole branching substituent. The methyl branching group is preferably located on the first, second, or third carbon atom (counting from the halogenated carbon atom), more preferably on the first or second carbon atom. Examples of $R^1$ include an isopropyl group, a 2-methylpropyl group, and a 1-methylpropyl group.

The lateral methoxy group present in the core is in a position to restrict the rotation of the ester carbonyl adjacent to the chiral carbon to which the halogen atom is attached. The compounds of the present invention generally exhibit a chiral smectic C phase over a temperature range that is at least 60° C. wide, preferably at least 70° C. wide.

All of the compounds of the present invention can be made by conventional synthesis steps known in the art, without undue experimentation, from known and/or commercially available starting materials. The compounds of the present invention are comprised of the alkoxybiphenyl esters of vanillic acid in which the phenolic group has been esterified by the corresponding optically active haloalkyl acid. The group —C(X)$R^1$ can be conveniently obtained from the halo-analogues of optically active amino acids such as 1-valine, 1-leucine and 1-isoleucine. That is, the amino groups thereof can be replaced with a halogen by conventional reactions; i.e., by the use of diazonium chlorides. A preferred scheme for the synthesis of the compounds of the present invention is shown below with respect to inventive compounds [7] through [9] and is detailed in the following examples. Other compounds according to the present invention can be made by similar and/or analogous processes.

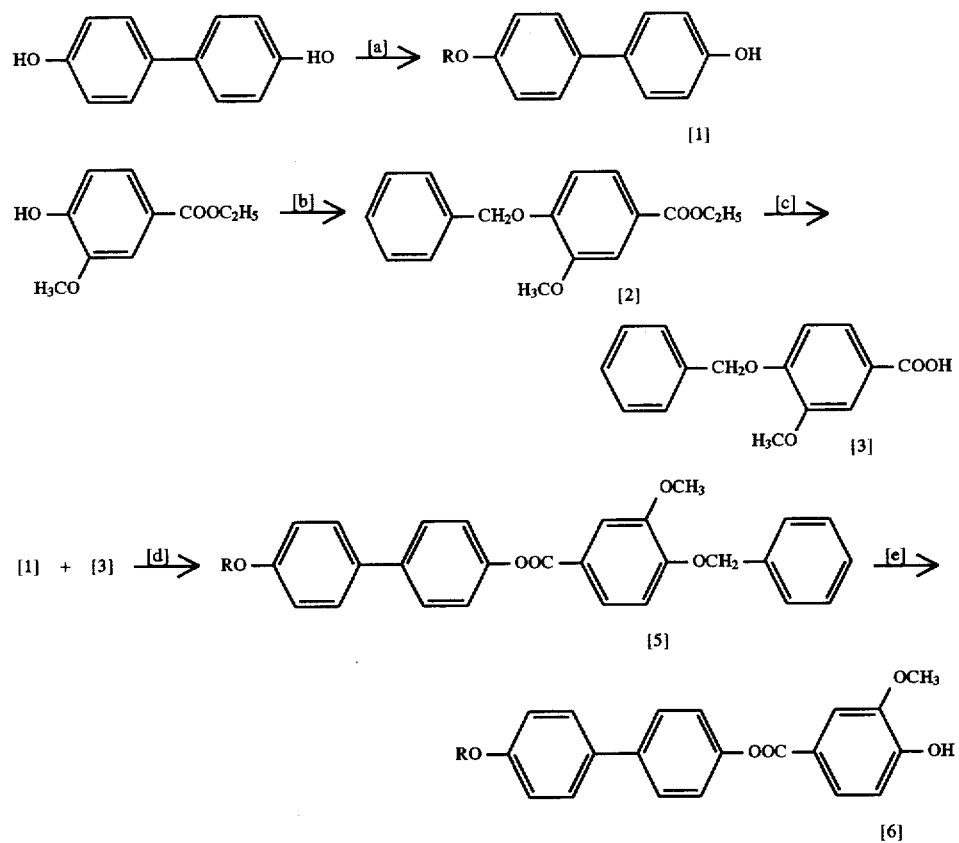

[a] Na/ethanol & alkylbromide,
[b] Na/ethanol & benzylbromide,
[c] KOH/aqueous ethanol,
[d] DMAP-pTS[4], DCC in methylene chloride,
[e] H$_2$—Pd/C in dioxan.

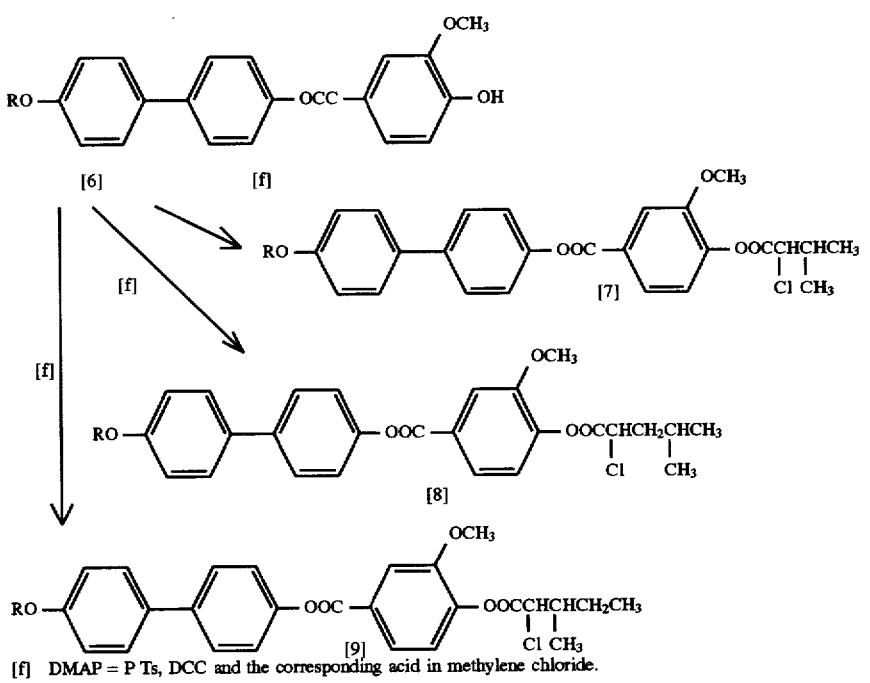

[f] DMAP = P Ts, DCC and the corresponding acid in methylene chloride.

Inventive compound [9] with two chiral carbons is isomeric to inventive compound [8] while compound [7] has the lower homologue of the chiral acid attached to it. Thus, a condensation of alkoxybiphenol and benzyloxy vanillic acid in the presence of 4-N,N'-Dimethylaminopyridinium 4'-toluenesulfonate and N,N'-dicyclohexylcarbodiimide in methylene chloride yielded the ester [5] which was subjected to hydrogenolysis with palladised charcoal in dioxane to obtain the precursor phenol [6]. The reaction products, wherein R is n-decyl, were characterized by proton magnetic resonance which are shown in FIGS. 1a–1g using a Bruker 200 MHz NMR and deuterated chloroform (CDCl$_3$) as the solvent.

The textures of the mesophases were seen under a polarizing microscope and transitions also studied by differential scanning calorimetry. It is seen that the intermediate ester [5] exhibits an enantiotropic nematic phase. The final compounds [7], [8], and [9] where R is n-decyl, all exhibit the desired chiral smectic C phase. In compounds [7] and [9] this phase is followed by smectic A and then the chiral nematic phases. In contrast compound [8] exhibits a smectic A phase after the C* phase and then goes directly into the isotropic liquid phase. When observed (without any surface treatment) through a polarizing microscope, a banded focal conic texture was seen for compound [7] and in other two compounds a Schlieren texture was obtained upon cooling the homeotropic smectic A phase.

Figure 2A:
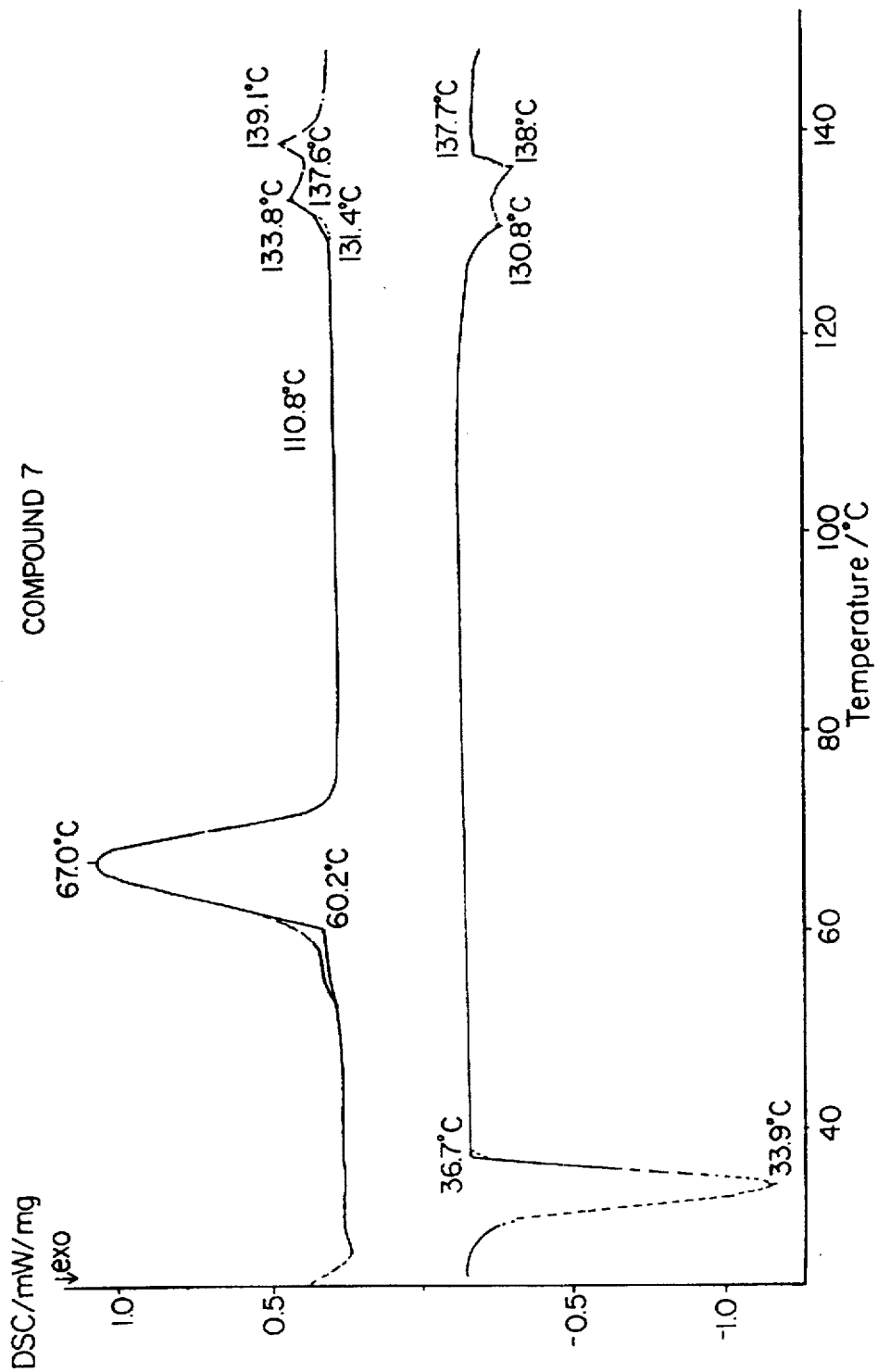

The differential calorimetric plots of compounds [7], [8], and [9] are shown in FIGS. 2a–2c and were obtained on a Netzsch instrument wherein the heating and cooling scans were each run at a rate of ten degrees per minute. The smectic C*-smectic A transition is present in the heating as well as cooling cycles. The chiral smectic C phase, which is seen to be the predominant phase, has an enantiotropic temperature range of about forty-five degrees and supercools to room temperature on average about forty degrees below the melting point of the compound. Thus, when the samples are cooled the chiral smectic C phase is seen to supercool to room temperature thereby providing a total phase range of more than seventy five degrees in the case of compounds [7] and [8] and about ninety-five degrees for compound [9].

Examples for the preparation of the decyl homologues are detailed below. However, it should be understood that these specific examples, while indicating preferred embodiments of the invention, are given by way of illustration only and are not intended to limit the scope of the present invention.

Step [A]

To a stirred solution of sodium ethoxide, prepared by addition of sodium (0.05 g atom) to absolute ethanol (200 ml), was added 4,4'-biphenol (0.05 mol) and the reaction mixture refluxed for one hour. This dark solution was then cooled to room temperature and 1-bromodecane (0.055 mol) was added to it. Refluxing was continued with stirring for a period of twenty four hours. Ethanol was then removed by distillation under reduced pressure and the residual reaction mixture was then poured into an ice-cold solution of 10% aqueous HCl (50 ml). The organic layer was extracted in ethyl acetate (2×100 ml). An insoluble solid floating in the ethyl acetate layer was filtered off. The clear combined organic layer was then washed with water (3×100 ml), dried over anhydrous sodium sulfate, filtered and the solvent evaporated. The solid obtained was stirred over cold petroleum ether and the ether layer decanted off. The solid was then crystallized from acetone and recrystallized twice from ethanol to yield the desired pure product [1] (52%) m.p. 147. (reported 149° C.) [V. Vill, Liquid Crystals, Landolt-Bornstein New Series, Group IV, Vol. 7a–7d, Ed. J. Thiem, Springer-Verlag 1992–4].

Step [B]

To a stirred solution of sodium ethoxide, prepared by addition of sodium (0.043 g atom) to absolute ethanol (150 ml), was added ethyl 4-hydroxy-3-methoxybenzoate (0.04 mol) and the reaction mixture refluxed for one hour. After cooling this to room temperature benzyl bromide (0.044 mol) was added to the clear solution. The reaction mixture was then refluxed for eighteen hours. After completion of the reaction, ethanol was removed under reduced pressure and the residue poured into ice cold water (60 ml). The organic portion was extracted twice into methylene chloride and the combined organic layer (200 ml.) was washed successively with 5% aqueous sodium hydroxide (5×60 ml), water (1×75 ml), dilute HCl (2×60 ml) and water (2×60 ml). The solution was then dried over anhydrous sodium sulfate and filtered. The solvent was removed to yield a white solid which was stirred over cold petroleum ether. The ether layer was decanted off and the product [2] obtained was crystallized from ethanol (83%) m.p. 80° C.

Step [C]

A mixture of ethyl 4-benzyloxy-3-methoxybenzoate (0.028 mol), potassium hydroxide (0.041 mol), water (4 ml) and ethanol (20 ml) was refluxed vigorously for four hours. The reaction mixture was then poured into excess of water (200 ml) and acidified with cold dilute HCl to yield a white precipitate which was crystallized from acetone and recrystallized from ethanol to yield the desired acid[3] (90%) m.p. 172° C.

Preparation of 4-N,N-Dimethylaminopyridinium-4'-toluenesulfonate

A warm solution of 4-N,N-dimethylaminopyridine (0.1 mol) in dry benzene was added to a stirred hot solution of dehydrated p-toluenesulfonic acid (0.11 mol) in dry benzene resulting in an immediate precipitation of white powder. The reaction mixture was then cooled, the product [4] filtered and dried (95%) m.p. 168° C. [Moore, J. S., and Stupp S. I., *Macromolecules* 1990, 23, 65].

Step [D]

To a stirred mixture of 4(4'-decyloxyphenyl)phenol (0.015 mol), 4-benzyloxy-3-methoxybenzoic acid (0.0155 mol) and 4-N,N-dimethylaminopyridinium-4'-toluenesulfonate (0.0076 mol) in methylene chloride (60 ml) was added N,N'-dicyclohexylcarbodiimide (0.225 mol) in methylene chloride (10 ml). The reaction mixture was continued to be stirred at room temperature for thirty six hours. It was then filtered, further diluted by addition of the solvent (50 ml) and washed successively with 5% aqueous NaOH (3×50 ml), water (1×50 ml), dilute HCl (1×50 ml) and water (2×50 ml). It was then dried over anhydrous sodium sulfate and the solid obtained after removal of the solvent was chromatographed on silica gel and eluted with a 30% mixture of chloroform in hexane. The pure solid obtained after evaporating the solvent was crystallized in acetone to yield ester [5] (78%) m.p. 132° C. [K 132 N 146 I].

Step [E]

A solution of 4',4"-decyloxybiphenyl 4-benzyloxy-3-methoxybenzoate (0.011 mol) in 1,4-dioxane (60 ml) containing 5% Palladised charcoal (2 g) was stirred vigorously in an atmosphere of hydrogen for twenty hours at room temperature. It was then filtered and the solvent distilled off under reduced pressure. The solid obtained was crystallized twice in ethanol to yield the desired product [6] (90%) m.p. 133° C.

Step [F]

Following a procedure similar to the one described for compound [5], esterification of 4',4"-decyloxybiphenyl 4-hydroxy-3-methoxybenzoate with [S]-2-chloro-3-methylbutanoic acid yielded [S]-4',4"-Decyloxybiphenyl 4-(2'''-chloro-3'''-methylbutanoyloxy)-3-methoxybenzoate [7], which was purified by column chromatography and crystallized from ethanol (yield: 75%) m.p. 67.0° C. mesophase transition temperatures (°C) and heats of transition. (J/g). K 67.0 (40.3) $S_c^*$ 110.8 (0.3) $S_A$ 133.8 (1.2) N* 139.1 (1.4) I.

The physical data of the cognate preparations of the other two target esters viz. [S]-4',4"-decyloxybiphenyl 4- (2'''-chloro-4'''-methylpentanoyloxy)-3-methoxybenzoate [8] and [2S, 3S]-4'4"-decyloxybiphenyl 4-(2'''-chloro-3'''-methylpentanoyloxy)-3-methoxybenzoate [9] are as follows.

Compound [8]

Yield, 78%, m.p. 69.5° C. mesophase transition temperatures (°C) and heats of transition. (J/g). K 69.3 (46.8) $S_c^*$ 109.0 (1.1) $S_A$ 117.8 (5.7) I.

Compound [9]

Yield, 76%, m.p. 67.7° C. mesophase transition temperatures (° C) and heats of transition. (J/g). K 67.7 (54.5) $S_c^*$ 116.5 (0.3) $S_A$ 129.5 (0.6) N* 133.7 (1.9) I.

In all the compounds synthesized hereinabove, it was found that the smectic A phase is preceded by the chiral smectic C phase which is also the predominant phase. Further, the enantiotropic temperature range of this smectic C phase was about forty-five degrees and it was supercooled to room temperature about forty degrees below the melting point of the compound.

The compounds of the present invention are thus suitable for use in ferroelectric liquid crystal display devices. In particular, by replacing or supplementing the conventional chiral smectic C phase compounds of the prior art with the compounds of the present invention, a ferroelectric display having both a practical and a wide operating temperature range can be obtained. Further, the display will have good stability and long life owing to the excellent stability of the compounds of the present invention.

The invention having been thus described it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. A chiral aromatic compound represented by the formula

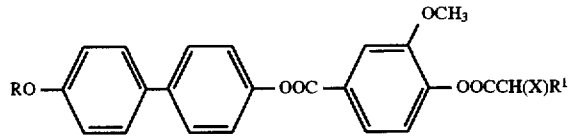

wherein R represents a hydrocarbon group having 1 to 14 carbon atoms, X is a halogen atom, and $R^1$ represents a branched alkyl group having 3 to 8 carbon atoms.

2. The chiral aromatic compound according to claim 1, wherein $R^1$ represents a singularly branched alkyl group.

3. The chiral aromatic compound according to claim 2, wherein $R^1$ has from 3 to 5 carbon atoms.

4. The chiral aromatic compound according to claim 3, wherein said singular branch in $R^1$ is a methyl group.

5. The chiral aromatic compound according to claim 1, wherein $R^1$ represents an isopropyl group.

6. The chiral aromatic compound according to claim 1, wherein $R^1$ represents a 2-methylpropyl group.

7. The chiral aromatic compound according to claim 1, wherein $R^1$ represents a 1-methylpropyl group.

8. The chiral aromatic compound according to claim 1, wherein R represents a normal alkyl chain having from six to twelve carbon atoms.

9. The chiral aromatic compound according to claim 1, wherein X is chlorine.

10. The chiral aromatic compound according to claim 9, wherein $R^1$ is a group selected from the group consisting of an isopropyl group, a 2-methylpropyl group, and a 1-methylpropyl group.

* * * * *